(12) United States Patent
Bradley et al.

(10) Patent No.: US 7,884,112 B2
(45) Date of Patent: Feb. 8, 2011

(54) PYRROLOPYRIDINE-2-CARBOXYLIC ACID HYDRAZIDES

(76) Inventors: Stuart Edward Bradley, Watlington Road, Oxford (GB) OX4 6LT; Revathy Perpetua Jeevaratnam, Watlington Road, Oxford (GB) OX4 6LT; Thomas Martin Krulle, Watlington Road, Oxford (GB) OX4 6LT; Martin James Procter, Watlington Road, Oxford (GB) OX4 6LT; Robert John Rowley, Watlington Road, Oxford (GB) OX4 6LT; Gerard Hugh Thomas, Watlington Road, Oxford (GB) OX4 6LT; Ana Valdesabril, Watlington Road, Oxford (GB) OX4 6LT ( * ) Notice: Subject to any disclaimer, the term of this patent is extended or adjusted under 35 U.S.C. 154(b) by 570 days.

(21) Appl. No.: 10/591,895

(22) Filed: Nov. 5, 2007

(65) Prior Publication Data

US 2008/0269277 A1 Oct. 30, 2008

Related U.S. Application Data

(60) Provisional application No. 60/551,254, filed on Mar. 8, 2004.

(51) Int. Cl.
*A61K 31/437* (2006.01)
*C07D 471/04* (2006.01)
(52) U.S. Cl. ...................... 514/300; 546/113
(58) Field of Classification Search ........... None
See application file for complete search history.

(56) References Cited

U.S. PATENT DOCUMENTS

| | | |
|---|---|---|
| 5,346,907 A | 9/1994 | Kerwin |
| 5,618,792 A | 4/1997 | Gyorkos |
| 5,618,825 A | 4/1997 | Baldwin |
| 5,672,582 A | 9/1997 | Veber |
| 5,710,153 A | 1/1998 | Ohmoto |
| 5,756,810 A | 5/1998 | Baldwin |
| 5,821,241 A | 10/1998 | Claremon |
| 5,869,455 A | 2/1999 | Gyorkos |
| 5,885,967 A | 3/1999 | Schacht |
| 5,952,322 A | 9/1999 | Hoover |
| 6,001,811 A | 12/1999 | Gyorkos |
| 6,034,067 A | 3/2000 | Grootenhuis |
| 6,037,325 A | 3/2000 | Gyorkos |
| 6,090,787 A | 7/2000 | Schacht |
| 6,107,309 A | 8/2000 | Bhatnagar |
| 6,107,329 A | 8/2000 | Hoover |
| 6,124,277 A | 9/2000 | Schacht |
| 6,150,387 A | 11/2000 | Bohme et al. |
| 6,174,887 B1 | 1/2001 | Haruta |
| 6,277,877 B1 | 8/2001 | Hoover |
| 6,297,269 B1 | 10/2001 | Hulin |
| 6,399,601 B1 | 6/2002 | Dubois |
| 6,410,684 B1 | 6/2002 | Adang |
| 6,420,561 B1 | 7/2002 | Haruta |
| 6,432,921 B2 | 8/2002 | Adang |
| 6,455,529 B1 | 9/2002 | Gante |
| 2003/0004162 A1 | 1/2003 | Treadway |
| 2005/0054696 A1 | 3/2005 | Nakamura |

FOREIGN PATENT DOCUMENTS

| | | |
|---|---|---|
| EP | 0254545 B1 | 7/1987 |
| EP | 0345990 A2 | 5/1989 |
| EP | 0978276 B1 | 4/1995 |
| EP | 0832066 B1 | 6/1995 |
| EP | 0810221 A1 | 2/1996 |
| EP | 0846464 A2 | 3/1997 |
| EP | 1101759 A1 | 7/1999 |
| EP | 1136071 A2 | 5/2000 |
| EP | 1179341 B1 | 5/2000 |
| EP | 1201239 A1 | 8/2000 |
| EP | 1177791 A2 | 7/2001 |
| GB | 2292149 A | 6/1994 |
| WO | 9636595 A1 | 5/1996 |
| WO | 9639384 A1 | 12/1996 |
| WO | 9717985 A1 | 5/1997 |
| WO | 9731016 A2 | 8/1997 |
| WO | 9825617 A1 | 6/1998 |
| WO | 0043384 A1 | 7/2000 |
| WO | 0069815 A1 | 11/2000 |
| WO | 0076970 A2 | 12/2000 |
| WO | 0102424 A2 | 1/2001 |

(Continued)

OTHER PUBLICATIONS

International Preliminary Report on Patentability in PCT/GB2005/000885, 2005.

(Continued)

*Primary Examiner*—Zinna N Davis
(74) *Attorney, Agent, or Firm*—Mintz Levin Cohn Ferris Glovsky and Popeo, P.C.; Ivor R. Elrifi

(57) ABSTRACT

Compounds of Formula (I) or pharmaceutically acceptable salts thereof, are inhibitors of glycogen phosphorylase and are useful in the prophylactic or therapeutic treatment of diabetes, hyperglycemia, hypercholesterolemia, hyperinsulinemia, hyperlipidemia, hypertension, atherosclerosis or tissue ischemia e.g. myocardial ischemia, or as cardioprotectants or inhibitors of abnormal cell growth.

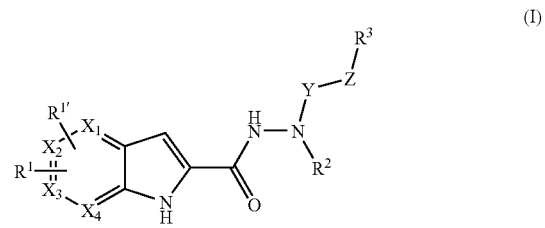

15 Claims, No Drawings

FOREIGN PATENT DOCUMENTS

| | | | |
|---|---|---|---|
| WO | 0132622 | A1 | 5/2001 |
| WO | 0155146 | A1 | 8/2001 |
| WO | 0162775 | A2 | 8/2001 |
| WO | 0168055 | A1 | 9/2001 |
| WO | 0194310 | A1 | 12/2001 |
| WO | 0196346 | A1 | 12/2001 |
| WO | 0216314 | A1 | 2/2002 |
| WO | 0220475 | A2 | 3/2002 |
| WO | 0226697 | A2 | 4/2002 |
| WO | 0240469 | A1 | 5/2002 |
| WO | 0246159 | A1 | 6/2002 |
| WO | WO 03/037864 | A * | 5/2003 |
| WO | 2004104001 | A2 | 12/2004 |
| WO | 2004113345 | A1 | 12/2004 |
| WO | WO 2004/104001 | A * | 12/2004 |

OTHER PUBLICATIONS

Written Opinion of the International Search Authority in PCT/GB2005/000885, 2005.

International Search Report in PCT/GB2005/000885, 2005.

\* cited by examiner

PYRROLOPYRIDINE-2-CARBOXYLIC ACID HYDRAZIDES

This is a 35 U.S.C. 371 application of PCT/GB2005/000885 which claims the benefit of U.S. patent application Ser. No. 60/551,254 filed Mar. 8, 2004.

BACKGROUND OF THE INVENTION

The present invention is directed to pyrrolopyridine-2-carboxylic acid hydrazides. In particular, the present invention is directed to pyrrolopyridine-2-carboxylic acid hydrazides that are inhibitors of glycogen phosphorylase.

Insulin dependent Type I diabetes and non-insulin dependent Type II diabetes continue to present treatment difficulties even though clinically accepted regimens that include diet, exercise, hypoglycemic agents, and insulin are available. Treatment is patient dependent therefore there is a continuing need for novel hypoglycemic agents, particularly ones that may be better tolerated with fewer adverse effects.

The liver and certain other organs produce glucose (thereby raising the blood sugar level) by breaking down glycogen or by synthesizing glucose from small molecule precursors. The breakdown of glycogen is catalyzed by glycogen phosphorylase enzyme. Accordingly, inhibiting glycogen phosphorylase ("GP") may lower the elevated blood sugar level in diabetic patients.

Similarly, hypertension and its associated pathologies such as, for example, atherosclerosis, lipidemia, hyperlipidemia and hypercholesterolemia have been associated with elevated insulin levels (hyperinsulinemia), which can lead to abnormal blood sugar levels. Furthermore, myocardial ischemia can result. Such maladies may be treated with hypoglycemic agents, including compounds that inhibit glycogen phosphorylase. Accordingly, it is accepted that compounds that inhibit glycogen phosphorylase (see, for example, U.S. Pat. No. 6,297,269) are useful in the treatment of diabetes, hyperglycemia, hypercholesterolemia, hyperinsulinemia, hyperlipidemia, atherosclerosis or myocardial ischemia. Nevertheless, it would be desirable to obtain other novel compounds that inhibit glycogen phosphorylase.

R. Kurukulasuriya, J. T. Link, et al., *Current Medicinal Chem.*, 10:99-121 (2003) describes "Prospects for Pharmacologic Inhibition of Hepatic Glucose Production." R. Kurukulasuriya, J. T. Link, et al., *Current Medicinal Chem.*, 10: 123-153 (2003) describes "Potential Drug Targets and Progress Towards Pharmacologic Inhibition of Hepatic Glucose Production."

U.S. Pat. No. 6,297,269 and European Patent No. EP 0832066 describes substituted N-(indole-2-carbonyl)amides and derivatives as glycogen phosphorylase inhibitors. U.S. Pat. Nos. 6,107,329 and 6,277,877 describe substituted N-(indole-2-carbonyl)glycinamides and derivatives as glycogen phosphorylase inhibitors. U.S. Pat. No. 6,399,601 describes bicyclic pyrrolyl amides as glycogen phosphorylase inhibitors. International Patent Publication No. WO 03/037864 describes indole derivatives as glycogen phosphorylase inhibitors. European Patent Application Nos. EP 0978276 and EP 1136071 describe inhibitors of human glycogen phosphorylase and their use. International Patent Publication No. WO 01/68055 describes glycogen phosphorylase inhibitors. U.S. Pat. No. 5,952,322 describes a method of reducing non-cardiac ischemial tissue damage using glycogen phosphorylase inhibitors.

European Patent Application No. EP 1177791 describes the use of glycogen phosphorylase inhibitors to inhibit abnormal cell growth, e.g. in the treatment of cancer and hyperproliferative disorders.

International Patent Publication No. WO 04/104001 (published after the priority date of the present application) discloses pyrrolopyridine-2-carboxylic acid amide inhibitors of glycogen phosphorylase.

International Patent Publication No. WO 04/113345 (published after the priority date of the present application) discloses fused pyrrole compounds as inhibitors of glycogen phosphorylase.

International Patent Publication No. WO 01/55146 describes arylamidines. International Patent Publication No. WO 01/62775 describes antiarrhythmic peptides. International Patent Publication No. WO 01/96346 describes tricyclic compounds. International Patent Publication No. WO 02/16314 describes substituted polyamine compounds. International Patent Publication No. WO 02/20475 describes serine protease activity inhibitors. International Patent Publication No. WO 02/40469 describes bombesin receptor antagonists. International Patent Publication No. WO 02/46159 describes guanidine and amidine derivatives. International Patent Publication No. WO 00/69815 describes ureido-substituted cyclic amine derivatives.

International Patent Publication No. WO 00/43384 describes aromatic heterocyclic compounds. International Patent Publication Nos. WO 02/26697 and WO 00/76970 describe aromatic derivatives. International Patent Publication No. WO 01/32622 describes indoles. European Patent Application No. EP 1101759 describes phenylazole compounds. European Patent Application No. EP 1179341 describes cyclic amino compounds. U.S. Pat. No. 6,037,325 describes substituted heterocyclic compounds. U.S. Pat. No. 5,672,582 describes 4-substituted cyclohexylamine derivatives. European Patent Application No. EP 1201239 describes cyclic amine CCR3 antagonists. International Patent Publication No. WO 98/25617 describes substituted arylpiperazines. U.S. Pat. No. 5,756,810 describes preparing 3-nitro benzoate compounds.

U.S. Pat. No. 5,710,153 describes tetrazole compounds. U.S. Pat. Nos. 6,174,887 and 6,420,561 describe amide compounds. S. P. Hiremath et al., *Acta Ciencia Indica*, XVIII:397 (1992) describes the synthesis and biological activities of indolylthiosemicarbazides and semicarbazides. International Patent Publication No. WO 96/36595 describes 3,4-disubstituted phenylsulfonamides. U.S. Pat. No. 5,618,825 describes combinatorial sulfonamide libraries. European Patent Application No. EP 0810221 describes oxygen-containing heterocyclic derivatives. European Patent Application No. 0345990 describes polypeptide compounds. European Patent Application No. 0254545 describes diamine compounds.

International Patent Publication No. WO 97/31016 describes inhibitors of SH2-mediated processes. U.S. Pat. No. 6,034,067 describes serine protease inhibitors. International Patent Publication No. WO 97/17985 and U.S. Pat. No. 6,107,309 describe hemoregulatory compounds. U.S. Pat. No. 6,432,921 describes thrombin inhibitors. U.K. Patent Application No. GB 2292149 describes peptide inhibitors of pro-interleukin-1β converting enzyme. U.S. Pat. No. 5,821,241 describes fibrinogen receptor antagonists.

International Patent Publication No. WO 01/02424 describes peptide boronic acid compounds. U.S. Pat. Nos. 6,001,811, 5,869,455 and 5,618,792 describe oxadiazole, thiadiazole and triazole peptoids. U.S. Pat. Nos. 5,885,967, 6,090,787 and 6,124,277 describe thrombin inhibiting peptide derivatives. U.S. Pat. No. 6,455,529 describes adhesion receptor antagonists. U.S. Pat. No. 6,410,684 describes serine protease inhibitors.

International Patent Publication No. WO 01/94310 describes bis-heterocyclic alkaloids. U.S. Patent Publication No. 20030004162A1, European Patent Application No. EP 0846464 and International Patent Publication No. WO 96/39384 describe glycogen phosphorylase inhibitors. International Patent Publication No. WO 97/28798 describes pyrrolidine derivatives. U.S. Pat. No. 5,346,907 describes amino acid analogs.

SUMMARY OF THE INVENTION

Compounds of formula (I):

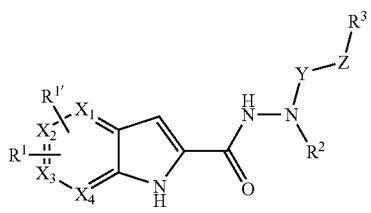

I or pharmaceutically acceptable salts thereof, are inhibitors of glycogen phosphorylase and are useful in the prophylactic or therapeutic treatment of diabetes, hyperglycemia, hypercholesterolemia, hyperinsulinemia, hyperlipidemia, hypertension, atherosclerosis or tissue ischemia e.g. myocardial ischemia, or as cardioprotectants or inhibitors of abnormal cell growth.

DETAILED DESCRIPTION OF THE INVENTION

The present invention is directed to a compound of formula (I):

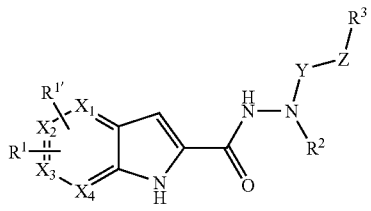

I or a pharmaceutically acceptable salt thereof, wherein:
one of $X_1$, $X_2$, $X_3$ and $X_4$ is N and the others are C;
Y is —C(O)—, —S(O)$_2$—, or —C(NH)—;
Z is $C_{1-4}$alkylene, oxygen, —(CH$_2$)$_m$O—, —O(CH$_2$)$_m$—, —NR—, —(CH$_2$)$_m$NR—, —NR(CH$_2$)$_m$—, —(CH$_2$)$_m$S(O)$_2$—, or a bond;
m is 1, 2, 3, or 4;
R is $C_{0-4}$alkyl, $C_{0-4}$alkylaryl, or $C_{0-4}$alkylhetaryl;
$R^1$ and $R^{1'}$ are each independently, halogen, hydroxy, cyano, $C_{0-4}$alkyl, $C_{1-4}$alkoxy, fluoromethyl, difluoromethyl, trifluoromethyl, ethenyl, or ethynyl;
$R^2$ is $C_{0-4}$alkyl, COOR$^6$, COR$^6$, $C_{1-4}$alkoxyC$_{1-4}$alkyl-, hydroxyC$_{0-4}$alkyl-, cycloalkylC$_{0-4}$alkyl-, arylC$_{0-4}$alkyl-, or hetarylC$_{0-4}$alkyl-, wherein any of the aryl or hetaryl rings are optionally substituted with 1-2 independent halogen, cyano, $C_{1-4}$alkyl, $C_{1-4}$alkoxy, —N(C$_{0-4}$alkyl)(C$_{0-4}$alkyl), —SO$_2$ (C$_{1-4}$ alkyl, —SO$_2$N(C$_{0-4}$alkyl)(C$_{0-4}$alkyl), hydroxy, fluoromethyl, difluoromethyl, or trifluoromethyl substituents;
$R^3$ is hydrogen, —COOC$_{0-4}$alkyl, $C_{1-4}$alkoxy, $C_{1-4}$alkyl, arylC$_{1-4}$alkylthio-, —C$_{0-4}$alkylaryl, —C$_{0-4}$alkylhetaryl, —C$_{0-4}$alkylcycloalkyl, or —C$_{0-4}$alkylheterocyclyl, wherein any of the rings is optionally substituted with 1-3 independent halogen, cyano, $C_{1-4}$alkyl, fluoromethyl, difluoromethyl, trifluoromethyl, —C$_{0-4}$alkylNHC(O)O(C$_{1-4}$alkyl), —C$_{0-4}$alkylNR$^7$R$^8$, —C(O)R$^9$, $C_{1-4}$alkoxyC$_{0-4}$alkyl-, —COOC$_{0-4}$alkyl, —C$_{0-4}$alkylNHC(O)R$^9$, —C$_{0-4}$alkylC(O)N(R$^{10}$)$_2$, —C$_{1-4}$alkoxyC$_{1-4}$alkoxy, hydroxyC$_{0-4}$alkyl-, —NHSO$_2$R$^{10}$, —SO$_2$(C$_{1-4}$alkyl), —SO$_2$NR$^{11}$R$^{12}$, 5- to 6-membered heterocyclyl, phenylC$_{0-2}$alkoxy, or phenylC$_{0-2}$alkyl substituents, wherein phenyl is optionally substituted with 1-2 independent halogen, cyano, $C_{1-4}$alkyl, $C_{1-4}$alkoxy, —N(C$_{0-4}$alkyl)(C$_{0-4}$alkyl), —SO$_2$C$_{1-4}$alkyl, —SO$_2$N(C$_{0-4}$alkyl)(C$_{0-4}$alkyl), hydroxy, fluoromethyl, difluoromethyl, or trifluoromethyl substituents, or two bonds on a ring carbon of the heterocyclyl group optionally can form an oxo (=O) substituent;
or $R^3$ is —NR$^4$(—C$_{0-4}$alkylR$^5$);
$R^4$ is $C_{0-3}$alkyl, —C$_{2-3}$alkyl-NR$^7$R$^8$, $C_{3-6}$cycloalkyl optionally substituted by hydroxyC$_{0-4}$alkyl- further optionally substituted by hydroxy, $C_{1-2}$alkoxyC$_{2-4}$alkyl-, or $C_{1-2}$alkyl-S(O)$_n$—C$_{2-3}$alkyl-;
n is 0, 1, or 2;
$R^5$ is hydrogen, hydroxyC$_{2-3}$alkyl-, $C_{1-2}$alkoxyC$_{0-4}$alkyl-, or aryl, hetaryl, or heterocyclyl;
wherein a heterocyclic nitrogen-containing $R^5$ ring optionally is mono-substituted on the ring nitrogen with $C_{1-4}$alkyl, benzyl, benzoyl, $C_{1-4}$alkyl-C(O)—, —SO$_2$C$_{1-4}$alkyl, —SO$_2$N(C$_{0-4}$alkyl)(C$_{0-4}$alkyl), $C_{1-4}$alkoxycarbonyl, or aryl (C$_{1-4}$alkoxy)carbonyl; and wherein the $R^5$ rings are optionally mono-substituted on a ring carbon with halogen, cyano, $C_{1-4}$alkyl-C(O)—, $C_{1-4}$alkyl-SO$_2$—, $C_{1-4}$alkyl, $C_{1-4}$alkoxy, hydroxy, —N(C$_{0-4}$alkyl)(C$_{0-4}$alkyl), hydroxyC$_{0-4}$alkyl-, or $C_{0-4}$alkylcarbamoyl-, provided that no quaternised nitrogen is included; or two bonds on a ring carbon of the heterocyclyl group optionally can form an oxo (=O) substituent;
$R^6$ is $C_{1-4}$alkyl, aryl, or hetaryl;
$R^7$ and $R^8$ are independently $C_{0-4}$alkyl, $C_{3-6}$cycloalkyl, or CO(C$_{1-4}$alkyl);
$R^9$ is $C_{0-4}$alkyl, or $C_{3-6}$cycloalkyl;
$R^{10}$ is $C_{0-4}$alkyl, or $C_{3-6}$cycloalkyl; and
$R^{11}$ and $R^{12}$ are independently $C_{0-4}$alkyl or together with the nitrogen to which they are attached may form a 4- to 6-membered heterocycle;
provided there are no nitrogen-oxygen, nitrogen-nitrogen, oxygen-oxygen or nitrogen-halogen bonds in the grouping —Y-Z-R$^3$.

The molecular weight of the compounds of formula (I) is preferably less than 800, more preferably less than 600.

$X_3$ is preferably N.

Y is preferably —C(O)— or —S(O)$_2$—.

Z is preferably a $C_{1-4}$alkylene, oxygen, —(CH$_2$)$_m$O—, —NR— or a bond. More preferably Z is a bond.

R is preferably $C_{0-4}$alkyl.

$R^1$ and $R^{1'}$ are preferably each independently, hydrogen, halogen or cyano. More preferably one of $R^1$ and $R^{1'}$ is hydrogen and the other is halogen, e.g. chloro. More preferably one of $R^1$ and $R^{1'}$ is hydrogen and the other is 5-chloro.

$R^2$ is preferably $C_{0-4}$alkyl. More preferably $R^2$ is hydrogen.

$R^3$ is preferably hydrogen, —NR$^4$(—C$_{0-4}$alkylR$^5$), aryl, hetaryl, or heterocyclyl wherein any of the rings is optionally substituted as described above for formula (I).

$R^4$ is preferably hydrogen.

Specific compounds of the invention which may be mentioned are those included in the examples and pharmaceutically acceptable salts thereof.

While the preferred groups for each variable have generally been listed above separately for each variable, preferred compounds of this invention include those in which several or each variable in formula (I) is selected from the preferred, more preferred, most preferred, especially or particularly listed groups for each variable. Therefore, this invention is intended to include all combinations of preferred, more preferred, most preferred, especially and particularly listed groups.

As used herein, unless stated otherwise, "alkyl" as well as other groups having the prefix "alk" such as, for example, alkoxy, alkenyl, alkynyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains having at least one unsaturated carbon-carbon bond.

As used herein, for example, "$C_{0-4}$alkyl" is used to mean an alkyl having 0-4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group.

The term "cycloalkyl" means carbocycles containing no heteroatoms, and include mono-, bi-, and tricyclic saturated carbocycles, as well as fused and bridged systems. Such fused ring systems can include one ring that is partially or fully unsaturated, such as a benzene ring, to form fused ring systems, such as benzofused carbocycles. Cycloalkyl includes such fused ring systems as spirofused ring systems. Examples of cycloalkyl and carbocyclic rings include $C_{3-10}$cycloalkyl, e.g. $C_{3-8}$cycloalkyl, such as cyclopropyl, cyclobutyl, cyclopentyl, cyclohexyl, and decahydronaphthalene, adamantane, indanyl, 1,2,3,4-tetrahydronaphthalene and the like.

The term "halogen" includes fluorine, chlorine, bromine, and iodine atoms.

The term "aryl" is well known to chemists. The preferred aryl groups are phenyl and naphthyl, especially phenyl.

The term "hetaryl" is well known to chemists. The term includes 5- or 6-membered heteroaryl rings containing 1-4 heteroatoms chosen from oxygen, sulfur, and nitrogen in which oxygen and sulfur are not next to each other. Examples of such heteroaryl rings are furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The term "hetaryl" includes hetaryl rings with fused carbocyclic ring systems that are partially or fully unsaturated, such as a benzene ring, to form a benzofused hetaryl. For example, benzimidazole, benzoxazole, benzothiazole, benzofuran, quinoline, isoquinoline, quinoxaline, and the like.

Unless otherwise stated, the terms "heterocyclic ring" and "heterocyclyl" are equivalent, and include 4-8-membered saturated or partially saturated rings containing one or two heteroatoms chosen from oxygen, sulfur, and nitrogen. The sulfur and oxygen heteroatoms are not directly attached to one another. Any nitrogen heteroatoms in the ring may optionally be substituted with $C_{1-4}$alkyl. Examples of heterocyclic rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, N-methylpiperidine, azepane, azocane, [1,3]dioxane, oxazolidine, piperazine, homopiperazine, morpholine, thiomorpholine, 1,2,3,6-tetrahydropyridine and the like. Other examples of heterocyclic rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocyclic rings. The term "heterocyclic" also includes fused ring systems and can include a carbocyclic ring that is partially or fully unsaturated, such as a benzene ring, to form benzofused heterocycles. For example, 3,4-dihydro-1,4-benzodioxine, tetrahydroquinoline, tetrahydroisoquinoline and the like.

Compounds described herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above formula (I) is shown without a definitive stereochemistry at certain positions. The present invention includes all stereoisomers of formula (I) and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of formula (I) exists, the present invention includes any possible tautomers and pharmaceutically acceptable salts thereof, and mixtures thereof, except where specifically drawn or stated otherwise.

When the compound of formula (I) and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like Since the compounds of formula (I) are intended for pharmaceutical use they are preferably provided in substantially pure form, for example at least 60% pure, more suitably at least 75% pure especially at least 98% pure (% are on a weight for weight basis).

The compounds of formula (I) can be prepared as outlined in Scheme 1 below wherein $R^1$, $R^{1'}$, $R^2$, $R^3$, $X_1$, $X_2$, $X_3$, $X_4$, Y and Z are as defined above for formula (I):

Scheme 1

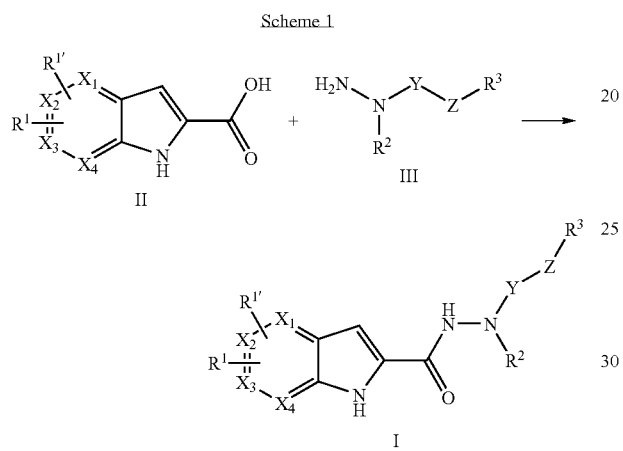

According to Scheme 1, the compounds of formula (I) may be prepared by coupling the appropriate pyrrolopyridine-2-carboxylic acid of formula (II) with the appropriate hydrazide of formula (III), wherein Y=C(O). Compounds of formula (II) can be obtained by the synthesis described in Scheme 7 below. Compounds of formula (III) are generally commercially available or are readily prepared by known techniques.

Typically, the compound of formula (II) is combined with compounds of formula (III) in the presence of a suitable coupling agent. Examples of suitable coupling reagents are 1-(3-dimethylaminopropyl)-3-ethylcarbodiimide hydrochloride/hydroxybenzotriazole (EDCI/HOBt), 1,1-carbonyldiimidazole (CDI), dicyclohexylcarbodiimide/hydroxybenzotriazole (DCC 35/HOBt), O-(1H-benzotriazol-1-yl)-N,N,N', N'-tetramethyluronium tetrafluoroborate (R. Knorr et al., *Tetrahedron Lett.*, 1989, 30, 1927-1930) and polymer supported carbodiimide-1-hydroxybenzotriazole (for representative procedures, see for example, Argonaut Technical Note 501 available from Argonaut Technologies, Inc., Foster City, Calif.).

The couplings are performed in an inert solvent, preferably an aprotic solvent at a temperature of about 0° C. to about 45° C. for about 1 to 72 h in the presence of a tertiary amine base such as diisopropylethylamine (DIPEA) or triethylamine. Exemplary solvents include acetonitrile, chloroform, dichloromethane, N,N-dimethylformamide (DMF) or mixtures thereof. Use of these coupling agents and appropriate selection of solvents and temperatures are known to those skilled in the art or can be readily determined from the literature. These and other exemplary conditions useful for coupling carboxylic acids are described in Houben-Weyl, Vol XV, part II, E. Wunsch, Ed., G. Thieme Verlag, 1974, Stuttgart, and M. Bodansky, Principles of Peptide Synthesis, Springer-Verlag, Berlin, 1984 and The Peptides, Analysis, Synthesis and Biology (Ed., E. Gross and J. Meienhofer), Vols 1-5, Academic Press NY 1979-1983.

The compounds of formula (I), wherein Y is C(O), may also be prepared according to Scheme 2 by coupling the appropriate hydrazide of formula (IV) with the appropriate carboxylic acid of formula (V). Examples of suitable coupling agents and conditions are as described above. Compounds of formula (IV) can be obtained by the synthesis described in Scheme 9 below. Compounds of formula (V) are commercially available or are readily prepared by known techniques.

Scheme 2

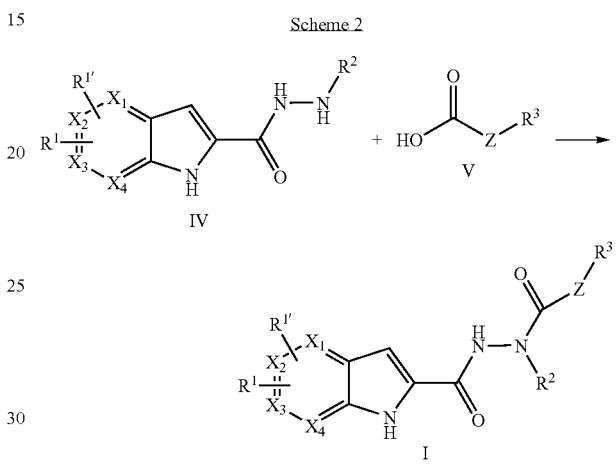

The compounds of formula (I), wherein Y is C(O) or —SO$_2$—, may be prepared according to Scheme 3 by mixing the appropriate hydrazide of formula (IV) with the appropriate acid chloride or sulfonyl chloride of formula (VI) in pyridine at room temperature, or alternatively in the presence of a tertiary amine base, e.g. diisopropylethylamine in a solvent such as 1,4-dioxane or THF at room temperature. Acid chlorides or sulfonyl chlorides of formula (VI) are commercially available or are readily prepared by known techniques.

Scheme 3

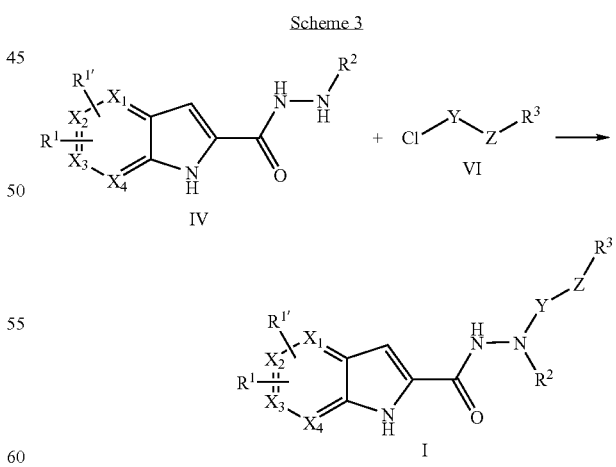

The compounds of formula (I), wherein Y is C(O) and Z is NH, may be prepared according to Scheme 4 by heating the appropriate hydrazide of formula (IV) with the appropriate isocyanate of formula (VII) under reflux in the presence of a tertiary amine base, e.g. diisopropylethylamine in a solvent such as 1,4-dioxane or toluene.

Scheme 4

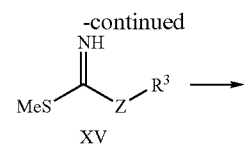

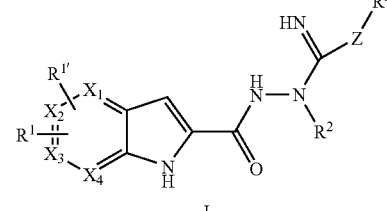

The compounds of formula (I), wherein Y is C(O), and Z is oxygen, may be prepared according to Scheme 5 by mixing the appropriate hydrazide of formula (IV) with the appropriate chloroformate of formula (VIII) in the presence of a tertiary amine base, e.g. triethylamine in a solvent such as dichloromethane.

Scheme 5

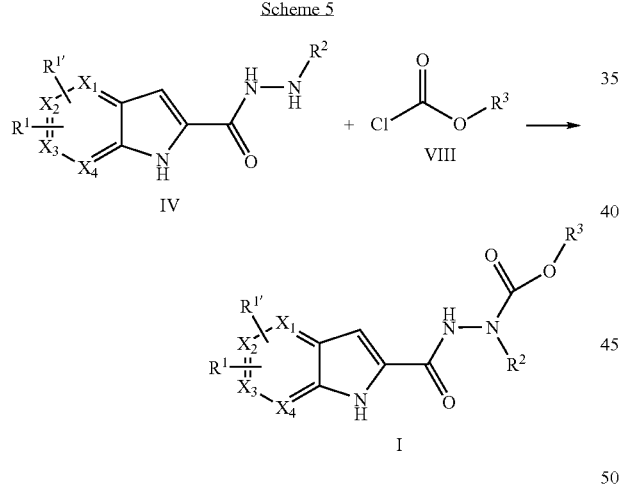

The compounds of formula (I), wherein Y is C(NH), may be prepared according to Scheme 6 by mixing the appropriate hydrazide of formula (IV) with the appropriate thioimidate of formula (XV) in a solvent such as ethanol or dimethylformamide.

Scheme 6

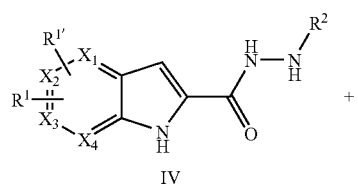

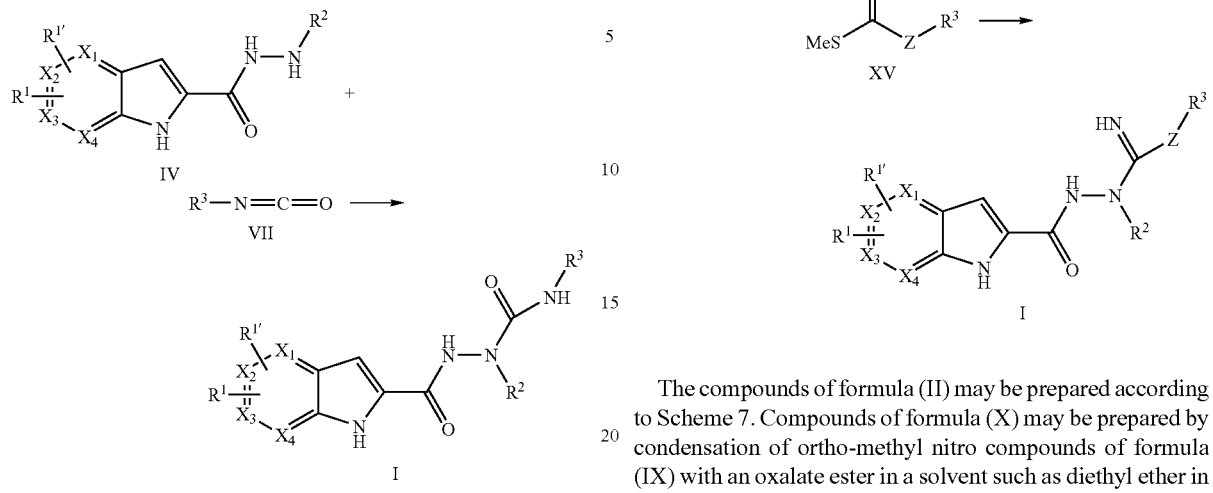

The compounds of formula (II) may be prepared according to Scheme 7. Compounds of formula (X) may be prepared by condensation of ortho-methyl nitro compounds of formula (IX) with an oxalate ester in a solvent such as diethyl ether in the presence of a base such as potassium ethoxide or DBU. Compounds of formula (XI) are prepared from compounds of formula (X) under reducing conditions, such as iron powder and ammonium chloride in ethanol at about 70° C., or by hydrogenation in ethanol using palladium catalysis at around 20° C. Compounds of formula (XI) undergo ester hydrolysis using aqueous alkali under standard conditions to give pyrrolopyridine-2-carboxylic acids of formula (II).

Scheme 7

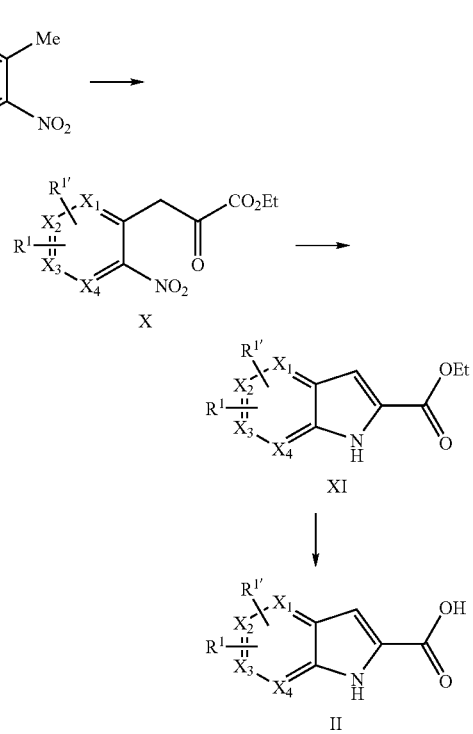

This three step process is similar to the Reissert indole synthesis (Reissert, Chemische Berichte 1897, 30, 1030). Conditions for accomplishing this sequence and references thereto, are described in Kermack et al., *J. Chem, Soc.,* 1921, 119, 1602; Cannon et al., J. Med. Chem. 1981, 24, 238; and Julian et al., in Heterocyclic compounds, Vol 3 (Wiley, New York, N.Y., 1962, R. C. Elderfield, Ed. p 18).

Alternatively, the compounds of formula (XI) wherein $X_2$ is nitrogen can be prepared as illustrated in Scheme 8.

Alternatively compounds of formula (IV), wherein $R^2$ is hydrogen, may be prepared (Scheme 9) by heating an ethyl ester of formula (XI) with compounds of formula (XIV), wherein $R^2$ is hydrogen, in a solvent such as ethanol under reflux for a period of 3 to 24 h.

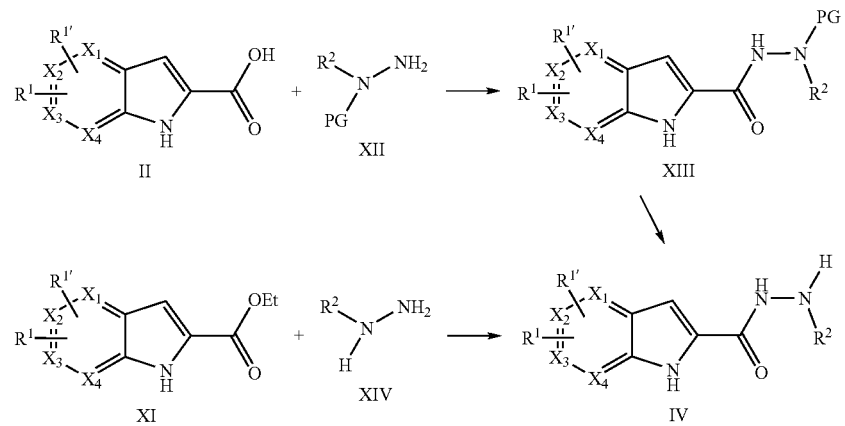

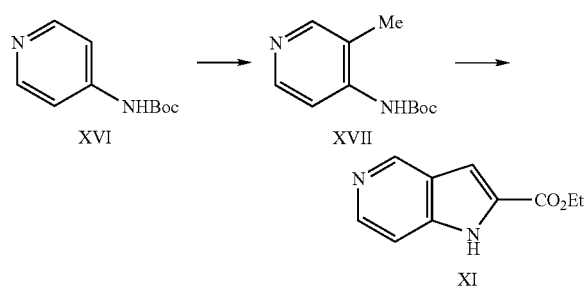

Deprotonation of compounds of formula (XVI) with an organolithium such as n-butyllithium in a suitable solvent such as THF, followed by quenching with methyl iodide gives compounds of formula (XVII). Such compounds can undergo further deprotonation with tert-butyllithium, in a suitable solvent such as THF, followed by quenching with diethyl oxalate and subsequent heating of the intermediate under reflux in hydrochloric acid, to give compounds of formula (XI).

Further details for the preparation of compounds of formula (II) can be found in WO04/104001 and the examples therein.

Formula (XIII) compounds may be prepared as described in Scheme 9 by coupling of carboxylic acids of formula (II) with hydrazines of formula (XII), wherein PG is a protecting group, e.g. Boc. Examples of suitable coupling agents and conditions are as described above for Scheme 1. Formula (IV) compounds may then be prepared by removal of the protecting group, e.g. where PG is Boc, under acidic conditions using for example trifluoroacetic acid in dichloromethane at temperatures of around 25° C. Formula (II) compounds are made as described above (Scheme 7) or are commercially available. Formula (XII) compounds are commercially available or are readily prepared by known techniques.

Further details for the preparation of the compounds of formula (I) are found in the examples.

The compounds of formula (I) may be prepared singly or as compound libraries comprising at least 2, for example 5 to 1,000 compounds and more preferably 10 to 100 compounds of formula (I). Compound libraries may be prepared by a combinatorial "split and mix" approach or by multiple parallel synthesis using either solution or solid phase chemistry, using procedures known to those skilled in the art.

During the synthesis of the compounds of formula (I), labile functional groups in the intermediate compounds, e.g. hydroxy, carboxy and amino groups, may be protected. The compounds of formulae (II) and (IV) may be protected in the 1-position e.g. with an arylmethyl, acyl, alkoxycarbonyl, sulfonyl or silyl group. The protecting groups may be removed at any stage in the synthesis of the compounds of formula (I) or may be present on the final compound of formula (I). A comprehensive discussion of the ways in which various labile functional groups may be protected and methods for cleaving the resulting protected derivatives is given in for example, Protective Groups in Organic Chemistry, T. W. Greene and P. G. M. Wuts, (1991) Wiley-Interscience, New York, $2^{nd}$ edition.

Any novel intermediates as defined above are also included within the scope of the invention.

The invention also provides a compound of formula (IV):

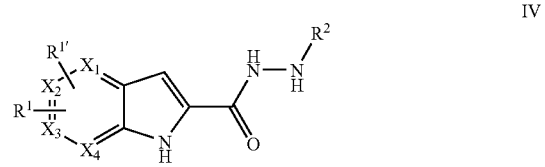

wherein $R^1$, $R^{1'}$, $R^2$, $X_1$, $X_2$, $X_3$ and $X_4$ are as defined above for formula (I), or a protected derivative thereof.

As indicated above the compounds of formula (I) are useful as inhibitors of glycogen phosphorylase, for the treatment of conditions such as diabetes, particularly Type II diabetes. For such use the compounds of formula (I) will generally be administered in the form of a pharmaceutical composition.

The invention also encompasses a pharmaceutical composition comprising a compound of formula (I), or a pharmaceutically acceptable salt thereof, in combination with a pharmaceutically acceptable carrier.

Preferably the composition is comprised of a pharmaceutically acceptable carrier and a non-toxic therapeutically effective amount of a compound of formula (I), or a pharmaceutically acceptable salt thereof.

Moreover, the invention also provides a pharmaceutical composition for the treatment of disease by inhibiting glycogen phosphorylase, resulting in the prophylactic or therapeutic treatment of diabetes, hyperglycemia, hypercholesteroleinia, hyperinsulinemia, hyperlipidemia, hypertension, atherosclerosis or tissue ischemia, e.g. myocardial ischemia, cardioprotection or inhibition of abnormal cell growth, comprising a pharmaceutically acceptable carrier and a non-toxic therapeutically effective amount of compound of formula (I), or a pharmaceutically acceptable salt thereof.

The pharmaceutical compositions may optionally comprise other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds of formula (I), or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous).

Thus, the pharmaceutical compositions can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound of formula (I), or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The compounds of formula (I), or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Moulded tablets may be made by moulding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, using a compound of formula (I), or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of formula (I), or pharmaceutically acceptable salts thereof, may also be prepared in powder or liquid concentrate form.

Generally, dosage levels on the order of 0.01 mg/kg to about 150 mg/kg of body weight per day are useful in the treatment of the above-indicated conditions, or alternatively about 0.5 mg to about 7 g per patient per day. For example, diabetes and hyperglycemia may be effectively treated by the administration of from about 0.01 to 50 mg of the compound per kilogram of body weight per day, or alternatively about 0.5 mg to about 3.5 g per patient per day. Similarly, hypercholesterolemia, hyperinsulinemia, hyperlipidemia, atherosclerosis or myocardial ischemia may be effectively treated, or cardioprotection or inhibition of abnormal cell growth achieved, by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of formula (I) may be used in the treatment of diseases or conditions in which glycogen phosphorylase plays a role.

Thus the invention also provides a method for the treatment of a disease or condition in which glycogen phosphorylase plays a role comprising a step of administering to a subject in need thereof an effective amount of a compound of formula (I), or a pharmaceutically acceptable salt thereof.

Diseases or conditions in which glycogen phosphorylase plays a role include diabetes (including Type I and Type II, impaired glucose tolerance, insulin resistance and diabetic complications such as neuropathy, nephropathy, retinopathy and cataracts), hyperglycemia, hypercholesterolemia, hyperinsulinemia, hyperlipidemia, hypertension, atherosclerosis, tissue ischemia e.g. myocardial ischemia, cardioprotection and abnormal cell growth e.g. cancer or hyperproliferative disorders.

The invention also provides a method for the treatment of hyperglycemia or diabetes, particularly Type II diabetes, comprising a step of administering to a subject in need thereof an effective amount of a compound of formula (I), or a pharmaceutically acceptable salt thereof.

The invention also provides a method for the prevention of diabetes in a human demonstrating pre-diabetic hyperglycemia or impaired glucose tolerance comprising a step of administering to a subject in need thereof an effective prophylactic amount of a compound of formula (I), or a pharmaceutically acceptable salt thereof.

In the treatment of diabetes, e.g. Type II diabetes, the compounds of the invention are particularly suited to night time dosing, optionally in combination with another antidiabetic agent.

The invention also provides a method for the treatment of hypercholesterolemia, hyperinsulinemia, hyperlipidemia, hypertension, atherosclerosis or tissue ischemia, or achieving cardioprotection or inhibition of abnormal cell growth, comprising a step of administering to a patient in need thereof an effective amount of a compound of formula (I), or a pharmaceutically acceptable salt thereof.

The invention also provides the use of a compound of formula (I), or a pharmaceutically acceptable salt thereof, in the treatment of a condition as defined above.

The invention also provides the use of a compound of formula (I), or a pharmaceutically acceptable salt thereof, in the manufacture of a medicament for the treatment of a condition as defined above.

In the methods of the invention the term "treatment" includes both therapeutic and prophylactic treatment.

The compounds of formula (I), or pharmaceutically acceptable salts thereof, may be administered alone or in combination with one or more other therapeutically active compounds. The other therapeutically active compounds may be for the treatment of the same disease or condition as the compounds of formula (I) or a different disease or condition. The therapeutically active compounds may be administered simultaneously, sequentially or separately.

The compounds of Formula (I) may be administered with other active compounds for the treatment of diabetes, for example insulin and insulin analogs, sulfonyl ureas and analogs, biguanides, α2 agonists, fatty acid oxidation inhibitors, α-glucosidase inhibitors, β-agonists, phosphodiesterase inhibitors, lipid lowering agents, antiobesity agents, amylin antagonists, lipoxygenase inhibitors, somostatin analogs, glucokinase activators, glucagon antagonists, insulin signalling agonists, PTP1B inhibitors, gluconeogenesis inhibitors, antilypolitic agents, GSK inhibitors, galanin receptor agonists, anorectic agents, CCK receptor agonists, leptin, CRF antagonists or CRF binding proteins.

The compounds of formula (I) may also be administered in combination with thyromimetic compounds, aldose reductase inhibitors, glucocorticoid receptor antagonists, NHE-1 inhibitors or sorbitol dehydrogenase inhibitors.

All publications, including, but not limited to, patents and patent application cited in this specification, are herein incorporated by reference as if each individual publication were specifically and individually indicated to be incorporated by reference herein as fully set forth.

The invention will now be described by reference to the following examples which are for illustrative purposes and are not to be construed as a limitation of the scope of the present invention.

EXAMPLES

Materials & Methods

Column chromatography was carried out on $SiO_2$ (40-63 mesh). LCMS data were obtained using a Waters Symmetry 3.5 $\mu C_{18}$ column (2.1×30.0 mm, flow rate=0.8 mL min$^{-1}$)

eluting with a (5% MeCN in H$_2$O)-MeCN solution containing 0.1% HCO$_2$H over 6 min & UV detection at 220 nm. Gradient information: 0.0-1.2 min: 100% (5% MeCN in H$_2$O); 1.2-3.8 min: Ramp up to 10% (5% MeCN in H$_2$O)-90% MeCN; 3.8-4.4 min: Hold at 10% (5% MeCN in H$_2$O)-90% MeCN; 4.4-5.5 min: Ramp up to 100% MeCN; 5.5-6.0 min: Return to 100% (5% MeCN in H$_2$O). The mass spectra were obtained employing an electrospray ionisation source in the positive (ES$^+$) ion mode. Mass directed purification was performed on a Micromass Platform LC with cone voltage 30 v, employing an electrospray ionisation source in the positive (ES$^+$) ion mode, Waters 996 Photodiode Array Detector (210-390 nm), Xterra Prep MS, C$_{18}$, 5μ 19×50 mm columns, and a mobile Phase of MeCN+0.1% Formic Acid/H$_2$0+5% MeCN+0.1% Formic Acid. NMR spectra were acquired at 27° C. on a Varian Mercury 400 spectrometer operating at 400 MHz or on a Bruker AMX2 500 spectrometer operating at 500 MHz.

Abbreviations & Acronyms

CDI: 1,1-carbonyldiimidazole; DIPEA: N,N-Diisopropylethylamine; DMF: N,N-Dimethylformamide; DMSO: Dimethylsulfoxide; EDCI: 1-(3-Dimethylaminopropyl)-3-ethylcarbodiimide hydrochloride; GP: Glycogen Phosphorylase; Glc: Glucose; G6P: Glucose-6-phosphate; G6PDH: Glucose-6-phosphate dehydrogenase; HATU: O-(7-Azabenzotriazol-1-yl)-N,N,N', N'-tetramethyluronium hexafluorophosphate; HOBt: 1-Hydroxybenzotriazole; PS: Polymer supported; rt: room temperature; RT: Retention time; THF: Tetrahydrofuran.

Intermediates

Preparation 1

6-Methyl-5-nitro-1H-pyridin-2-one

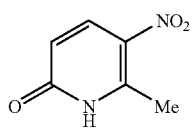

The title compound was prepared according to the method of Baumgarten and Su., (*J. Am. Chem. Soc.*, 1952, 74, 3828). δ$_H$ (d$_6$ DMSO): 2.62 (3H, s), 6.28 (1H, d), 8.10 (1H, d).

Preparation 2

2-Chloro-6-methyl-4-nitropyridine

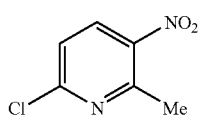

A suspension of 6-methyl-5-nitro-1H-pyridin-2-one (Preparation 1, 3.53 g, 22.9 mmol) in phosphorous oxychloride (20 mL) was heated to 115° C. for 3 h then allowed to cool to rt. The phosphorous oxychloride was removed in vacuo and the residue poured into iced water (100 mL). The mixture was quenched by addition of saturated sodium bicarbonate solution then the aqueous mixture was extracted with ethyl acetate (3×100 mL). The combined organics were washed with brine, dried (MgSO$_4$), filtered and concentrated in vacuo to give the title compound. δ$_H$ (CDCl$_3$): 2.86 (3H, s), 7.36 (1H, d), 8.27 (1H, d).

Preparation 3

3-(2-Chloro-5-nitropyridin-6-yl)-2-oxopropionic acid ethyl ester

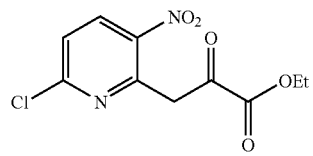

To a solution of potassium ethoxide (134 mg, 1.59 mmol) in diethyl ether (5 mL) and ethanol (1 mL) was added diethyl oxalate (218 μL, 1.59 mmol) in one portion and the resulting solution was stirred for 30 min at rt. 2-Chloro-6-methyl-5-nitropyridine (Preparation 2, 250 mg, 1.45 mmol) was added as a suspension in diethyl ether (2 mL) and stirring was continued for 17 h at rt. The mixture was filtered on a sinter, washing with cold diethyl ether. The collected precipitate was dissolved in glacial acetic acid then evaporated to dryness in vacuo to give the title compound. δ$_H$ (CDCl$_3$): 1.40 (3H, t), 4.38 (2H, q), 7.33 (1H, d), 7.37 (1H, s), 8.40 (1H, d).

Preparation 4

5-Chloro-1H-pyrrolo[3,2-b]pyridine-2-carboxylic acid ethyl ester

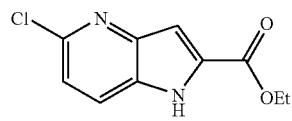

To a solution of 3-(2-chloro-5-nitropyridin-6-yl)-2-oxopropionic acid ethyl ester (Preparation 3, 1.53 g, 5.6 mmol) in THF (65 mL) and ethanol (30 mL) was added saturated aqueous ammonium chloride solution (30 mL) and the suspension was vigorously stirred at rt. Iron powder (1.95 g, 34.8 mmol) was added portionwise and the mixture was heated under reflux for 2 h then allowed to cool prior to filtration through a celite plug, and washed with warm THF. The mixture was concentrated under reduced pressure to give an aqueous suspension, which was filtered through a sinter, washing with water. The wet solid was washed with methanol and dried. The residue was adsorbed onto silica gel and purified via flash chromatography eluting with ethyl acetate/hexane (1:19) to give the title compound. δ$_H$ (CD$_3$OD): 1.42 (3H, t), 4.42 (2H, q), 7.15 (1H, s), 7.30 (1H, d), 7.89 (1H, d); m/z (ES$^+$)=225.03 [M+H]$^+$, RT=3.32 min.

Preparation 5

5-Chloro-1H-pyrrolo[3,2-b]pyridine-2-carboxylic acid

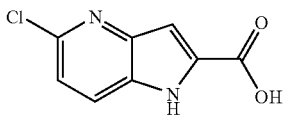

To a stirred solution of 5-chloro-1H-pyrrolo[3,2-b]pyridine-2-carboxylic acid ethyl ester (Preparation 4, 151 mg, 0.67 mmol) in ethanol (10 mL) was added sodium hydroxide (0.35 mL, 2M) and the stirred solution was heated to 70° C. for 2 h. The reaction mixture was allowed to cool to rt and left to stand for 16 h. The pH was adjusted to 4 by addition of glacial acetic acid, the solvents removed in vacuo to give a white solid, which was suspended in dichloromethane and filtered through a sinter, washing with additional dichloromethane. The filter cake was then washed with ethyl acetate (3×30 mL) and dried to give the title compound. $\delta_H$ (CD$_3$OD): 6.97 (1H, s), 7.17 (1H, d), 7.83 (1H, d); m/z (ES$^+$)=197 [M+H]$^+$; RT=2.82 min.

Preparation 6

3-(2-Chloro-5-nitropyridin-4-yl)-2-oxopropionic acid ethyl ester

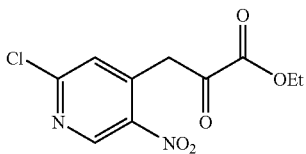

To a solution of potassium ethoxide (1.46 g, 17.4 mmol) in diethyl ether (80 mL) and ethanol (10 mL) under an argon atmosphere was added diethyl oxalate (2.4 mL, 17.4 mmol) and the mixture was stirred at rt for 30 min. A solution of 2-chloro-4-methyl-5-nitropyridine (3.0 g, 17.4 mmol) in diethyl ether (20 mL) was added resulting in the formation of a dark green precipitate. The reaction was stirred at rt for 15 h, cooled to 0° C., filtered and washed with cold diethyl ether to give a dark green solid. The solid was dissolved in water (200 mL) and acidified to pH 4 with acetic acid to give a precipitate. The solid was collected by filtration and dried to give the title compound. m/z (ES$^+$)=273 [M+H]$^+$.

Preparation 7

5-Chloro-1H-pyrrolo[2,3-c]pyridine-2-carboxylic acid ethyl ester

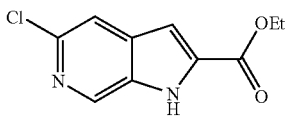

3-(2-Chloro-5-nitropyridin-4-yl)-2-oxopropionic acid ethyl ester (Preparation 6, 3.0 g, 11.0 mmol) was dissolved in ethanol (100 mL) and THF (50 mL). Iron powder (3.7 g, 66.0 mmol) and saturated ammonium chloride solution (50 mL) were added and the mixture was heated under reflux for 2 h. The mixture was cooled, filtered through celite and washed several times with ethyl acetate. The organic layers were combined, washed with brine (100 mL), dried (MgSO$_4$) and concentrated in vacuo to give the title compound. $\delta_H$ (CD$_3$OD): 1.42 (3H, t), 4.44 (2H, q), 7.15 (1H, s), 7.70 (1H, s), 8.59 (1H, s); m/z (ES$^+$)=225 [M+H]$^+$.

Preparation 8

5-Chloro-1H-pyrrolo[2,3-c]pyridine-2-carboxylic acid

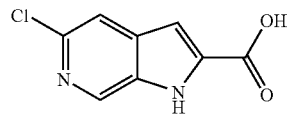

To a solution of 5-chloro-1H-pyrrolo[2,3-c]pyridine-2-carboxylic acid ethyl ester (Preparation 7, 1.78 g, 7.9 mmol) in ethanol (70 mL) was added sodium hydroxide solution (5.2 mL, 2M, 10.3 mmol) and the mixture was heated under reflux for 2 h. The solvent was removed in vacuo and the solid dissolved in water (150 mL) and acidified to pH 4 with acetic acid to give the title compound as a solid that was isolated by filtration. $\delta_H$ (CD$_3$OD): 7.13 (1H, s), 7.68 (1H, s), 8.58 (1H, s); m/z (ES$^+$)=197 [M+H]$^+$.

Preparation 9

Tetrahydropyran-4-carboxylic acid

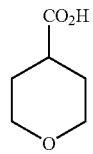

This compound was prepared by hydrolysis of the methyl ester according to the method of Spiegler and Goetz, *Ger. Offen.* (1987) DE 3536956 A1.

Preparation 10

5-Chloro-1H-pyrrolo[2,3-c]pyridine-2-carboxylic acid hydrazide

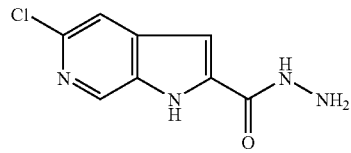

Route 1

N'-(tert-Butyloxycarbonyl)-5-chloro-1H-pyrrolo[2,3-c]pyridine-2-carboxylic acid hydrazide (EXAMPLE 25, 930 mg, 2.99 mmol) was suspended in a mixture of dichloromethane and trifluoroacetic acid (1:1, 20 mL). After 2 h the mixture was concentrated in vacuo and the oily residue was dissolved in water (200 mL). The aqueous layer was washed with ethyl acetate (2×50 mL) and concentrated in vacuo to give the title compound as its trifluoroacetic acid salt. $\delta_H$ (d$_6$ DMSO) 7.36 (1H, s), 7.83 (1H, s), 8.66 (1H, s), 9.3-10.8 (3H, br s), 11.8-12.2 (1H, br s), 12.6 (1H, s); m/z (ES$^+$)=211 [M+H]$^+$; RT=0.42 min.

Route 2

To a solution of 5-chloro-1H-pyrrolo[2,3-c]pyridine-2-carboxylic acid ethyl ester (Preparation 7, 880 mg, 3.91 mmol) in ethanol (30 mL) was added hydrazine monohydrate (4.0 mL, 78.22 mmol). The resulting solution was refluxed at 90° C. for 5 h. The reaction mixture was cooled to rt and the precipitate was filtered and dried to give the title compound. m/z (ES$^+$) 211 [M+H]$^+$; RT=1.65 min.

Example 1

5-Chloro-1H-pyrrolo[2,3-c]pyridine-2-carboxylic acid N'-(thiophene-2-yl-aminocarbonyl) hydrazide

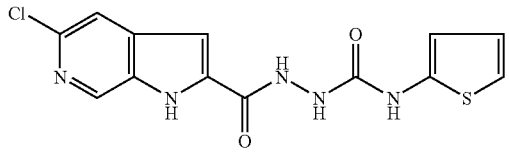

DIPEA (53 μL, 0.31 mmol) and thienyl isocyanate (40 μL, 0.32 mmol) were added to a suspension of 5-chloro-1H-pyrrolo[2,3-c]pyridine-2-carboxylic acid hydrazide trifluoroacetic acid salt (Preparation 10—route 1, 101 mg, 0.31 mmol) in a mixture of toluene and 1,4-dioxane (10 mL, 1:1). After stirring the mixture at 100° C. for 12 h, the reaction was allowed to cool to rt and the solvent was removed. The remaining oily residue was purified by flash chromatography on silica gel (toluene/acetone:2/1) to give the title compound. $\delta_H$ (CDCl$_3$): 6.60 (1H, d), 6.78 (1H, m), 6.84 (1H, d), 7.26 (1H, d), 7.82 (1H, s), 8.61 (2H, m), 9.97 (1H, s); m/z (ES$^+$)= 336 [M+H]$^+$; RT=2.97 min.

Example 2

Thiophene-3-carboxylic acid N'-(5-chloro-1H-pyrrolo[2,3-c]pyridine-2-carbonyl)hydrazide

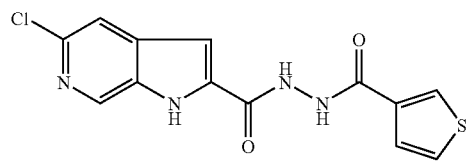

To a solution of 5-chloro-1H-pyrrolo[2,3-c]pyridine-2-carboxylic acid hydrazide trifluoroacetic acid salt (Preparation 10—route 1, 0.110 g, 0.34 mmol) in DMF (3 mL) was added DIPEA (170.0 μL, 1.02 mmol). To the stirred solution, HOBt (0.046 g, 0.34 mmol), EDCI (0.078 g, 0.41 mmol), DIPEA (120.0 μL, 0.68 mmol) and thiophene-3-carboxylic acid (0.044 g, 0.34 mmol) were added. The reaction mixture was stirred at rt for 16 h and then concentrated in vacuo to give an oil. On addition of ethyl acetate to the oil, a solid precipitated. The solid was filtered and dried to give the title compound. m/z (ES$^+$)=321 [M+H]$^+$; RT=2.84 min.

The coupling of the appropriate carboxylic acid with 5-chloro-1H-pyrrolo[2,3-c]-pyridine-2-carboxylic acid hydrazide, outlined in EXAMPLE 2, was also employed to prepare the compounds listed in Table 1 below.

TABLE 1

| EX. | Structure | Name | RT | m/z (ES$^+$) |
|---|---|---|---|---|
| 3 | 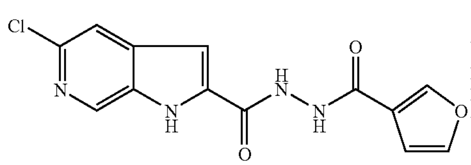 | Furan-3-carboxylic acid N'-(5-chloro-1H-pyrrolo[2,3-c]pyridine-2-carbonyl)hydrazide | 2.75 | 305 |
| 4 | 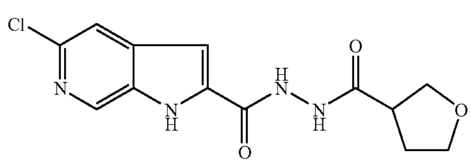 | Tetrahydrofuran-3-carboxylic acid N'-(5-chloro-1H-pyrrolo[2,3-c]pyridine-2-carbonyl)hydrazide | 2.59 | 309 |
| 5 | 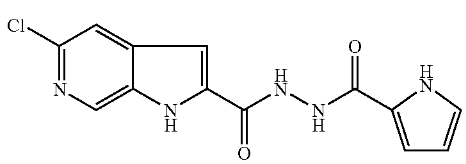 | 1H-Pyrrole-2-carboxylic acid N'-(5-chloro-1H-pyrrolo[2,3-c]pyridine-2-carbonyl)hydrazide | 2.77 | 304 |

TABLE 1-continued

| EX. | Structure | Name | RT | m/z (ES+) |
|-----|-----------|------|-----|-----------|
| 6 | 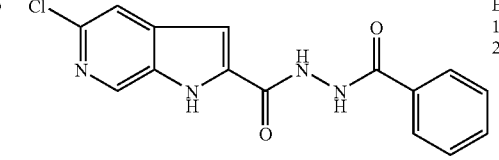 | Benzoic acid N'-(5-chloro-1H-pyrrolo[2,3-c]pyridine-2-carbonyl)hydrazide | 3.02 | 315 |

Example 7

Benzo[1,3]dioxole-5-carboxylic acid N'-(5-chloro-1H-pyrrolo[2,3-c]pyridine-2-carbonyl)hydrazide

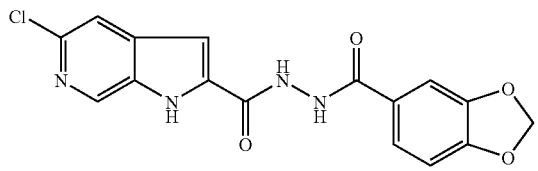

To a solution of 5-chloro-1H-pyrrolo[2,3-c]pyridine-2-carboxylic acid hydrazide (Preparation 10—route 2, 0.100 g, 0.48 mmol) in DMF (4 mL) was added HOBt (0.064 g, 0.48 mmol), EDCI (0.110 g, 0.58 mmol), DIPEA (200 μL, 0.96 mmol) and piperonylic acid (0.079 g, 0.48 mmol). The reaction mixture was stirred at rt for 16 h. The reaction mixture was poured into water (75 mL) and extracted with ethyl acetate (2×150 mL). The combined organic extract was washed with saturated sodium chloride (75 mL), dried (MgSO$_4$) and concentrated in vacuo to give a solid. The solid obtained was purified by recrystallisation from methanol to give the title compound. m/z (ES+)=359 [M+H]+; RT=2.92 min.

The coupling of the appropriate carboxylic acid with 5-chloro-1H-pyrrolo[2,3-c]-pyridine-2-carboxylic acid hydrazide, outlined above in EXAMPLE 7 was also employed to prepare the compounds listed in Table 2 below.

TABLE 2

| EX. | Structure | Name | RT | m/z (ES+) |
|-----|-----------|------|-----|-----------|
| 8 | 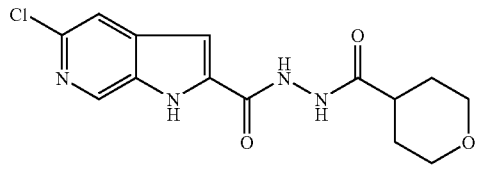 | Tetrahydropyran-4-carboxylic acid N'-(5-chloro-1H-pyrrolo[2,3-c]pyridine-2-carbonyl)hydrazide | 2.49 | 323 |
| 9 | 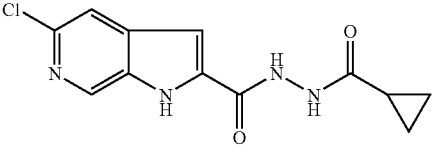 | Cyclopropane carboxylic acid N'-(5-chloro-1H-pyrrolo[2,3-c]pyridine-2-carbonyl)hydrazide | 2.42 | 279 |
| 10 | 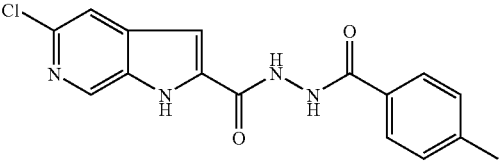 | 4-Methylbenzoic acid N'-(5-chloro-1H-pyrrolo[2,3-c]pyridine-2-carbonyl)hydrazide | 2.95 | 329 |
| 11 | 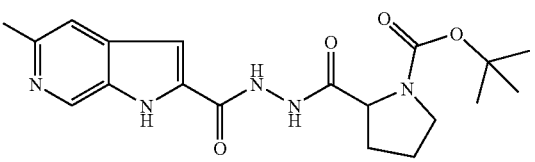 | 2(S)-[N'-5-Chloro-1H-pyrrolo[2,3-c]pyridine-2-carbonyl)-hydrazinocarbonyl]pyrrolidine-1-carboxylic acid tert-butyl ester | 3.01 | 408 |

TABLE 2-continued

| EX. | Structure | Name | RT | m/z (ES+) |
|---|---|---|---|---|
| 12 | 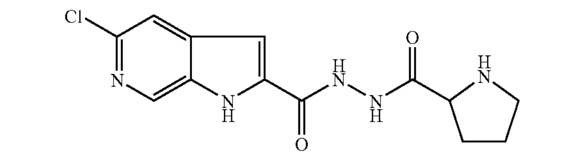 | Pyrrolidine-2(S)-carboxylic acid N'-(5-chloro-1H-pyrrolo[2,3-c]pyridine-2-carbonyl)hydrazide | 0.65 | 308 |
| 13 | 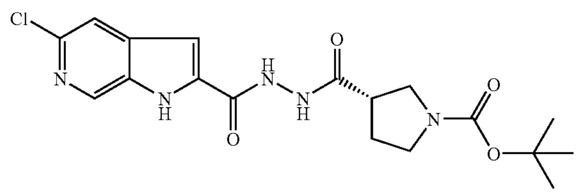 | 3(S)-N'-(5-Chloro-1H-pyrrolo[2,3-c]pyridine-2-carbonyl)-hydrazinocarbonyl] pyrrolidine-1-carboxylic acid tert-butyl ester | 3.32 | 408 |
| 14 | 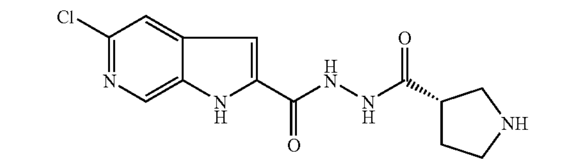 | Pyrrolidine-3(S)-carboxylic acid N'-(5-chloro-1H-pyrrolo[2,3-c]pyridine-2-carbonyl)hydrazide | 2.27 | 308 |

Example 15

Pyridine-3-carboxylic acid N'-(5-chloro-1H-pyrrolo[2,3-c]pyridine-2-carbonyl)hydrazide

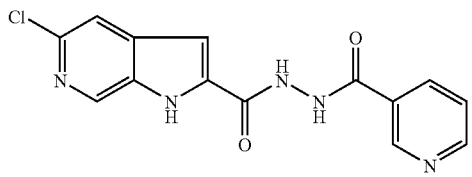

To a solution of nicotinic acid hydrazide (35 mg, 0.25 mmol) in DMF (5 mL) was added triethylamine (88 µL, 0.64 mmol), 5-chloro-1H-pyrrolo[2,3-c]pyridine-2-carboxylic acid (Preparation 8, 50 mg, 0.25 mmol), HOBt (34 mg, 0.25 mmol) and EDCI (50 mg, 0.28 mmol). The mixture was allowed to stir at rt for 16 h. The solvent was removed in vacuo and the residue was partitioned between water (100 mL) and ethyl acetate (100 mL). The organic layer was dried (MgSO$_4$) and concentrated in vacuo to give an oil, which was purified by flash chromatography on silica gel (dichloromethane/methanol, 9/1) to give the title compound. m/z (ES+)=316 [M+H]+; RT=2.62 min.

Example 16

5-Chloro-1H-pyrrolo[2,3-c]pyridine-2-carboxylic acid N'-phenylacetylhydrazide

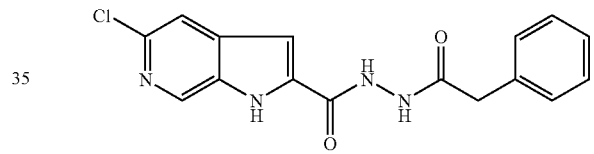

To a solution of 5-chloro-1H-pyrrolo[2,3-c]pyridine-2-carboxylic acid (Preparation 8, 50 mg, 0.25 mmol) in DMF (10 mL) was added DIPEA (89 µL, 0.51 mmol), HOBt (34 mg, 0.25 mmol), EDCI (63 mg, 0.33 mmol) and phenylacetic acid hydrazide (38 mg, 0.25 mmol) and the mixture was stirred at rt for 72 h. The reaction mixture was partitioned between water (50 mL) and ethyl acetate (3×30 mL). The combined organics were washed with brine (20 mL), dried (MgSO$_4$) and concentrated in vacuo. The crude material was chromatographed on silica gel eluting with methanol/dichloromethane (1:19) to give the title compound. m/z (ES+)=329 [M+H]+; RT=3.07 min.

The coupling of the appropriate hydrazide with 5-chloro-1H-pyrrolo[2,3-c]pyridine-2-carboxylic acid, outlined in EXAMPLE 16, was also employed to prepare the compounds listed in Table 3 below.

TABLE 3

| EX. | Structure | Name | RT (min) | m/z (ES+) |
|---|---|---|---|---|
| 17 | 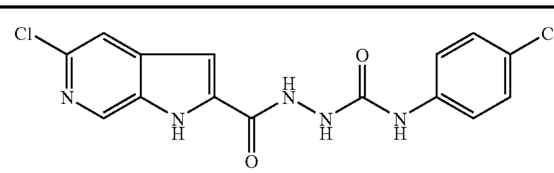 | 5-Chloro-1H-pyrrolo[2,3-c]pyridine-2-carboxylic acid N'-(4-chlorophenylaminocarbonyl)hydrazide | 3.30 | 364 |

TABLE 3-continued

| EX. | Structure | Name | RT (min) | m/z (ES+) |
|---|---|---|---|---|
| 18 | 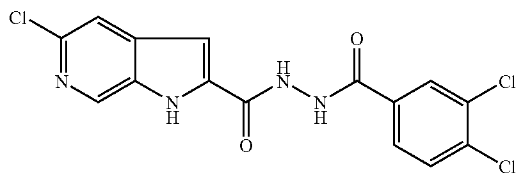 | 3,4-Dichlorobenzoic acid N'-(5-chloro-1H-pyrrolo[2,3-c]pyridine-2-carbonyl)hydrazide | 3.40 | 385 |
| 19 | 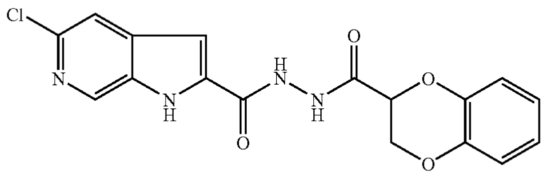 | 2,3-Dihydro-benzo[1,4]dioxine-2-carboxylic acid N'-(5-chloro-1H-pyrrolo[2,3-c]pyridine-2-carbonyl)hydrazide | 2.95 | 329 |
| 20 | 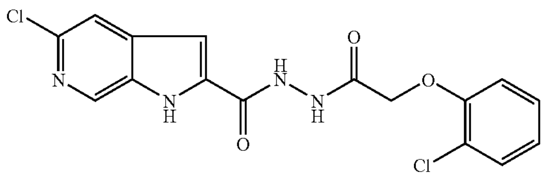 | 2-Chlorophenoxy acetyl N'-(5-chloro-1H-pyrrolo[2,3-c]pyridine-2-carbonyl)hydrazide | 3.30 | 379 |
| 21 | 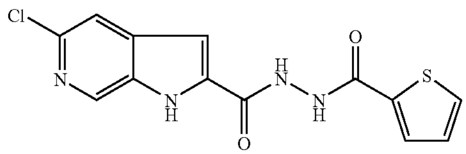 | Thiophene-2-carboxylic acid N'-(5-chloro-1H-pyrrolo[2,3-c]pyridine-2-carbonyl)hydrazide | 2.95 | 321 |
| 22 | 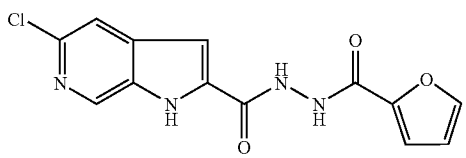 | Furan-2-carboxylic acid N'-(5-chloro-1H-pyrrolo[2,3-c]pyridine-2-carbonyl)hydrazide | 2.88 | 305 |
| 23 | 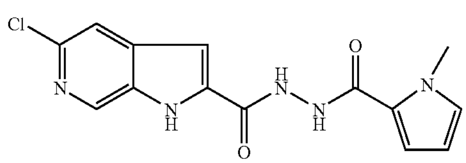 | 1-Methyl-1H-pyrrole-2-carboxylic acid N'-(5-chloro-1H-pyrrolo[2,3-c]pyridine-2-carbonyl)hydrazide | 3.05 | 318 |

Example 24

3,4-Dichlorobenzoic acid N'-(5-chloro-1H-pyrrolo[3,2-b]pyridine-2-carbonyl)hydrazide

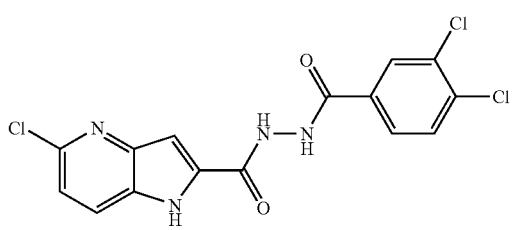

To a solution of 5-chloro-1H-pyrrolo[3,2-b]pyridine-2-carboxylic acid (Preparation 5, 20.0 mg, 0.10 mmol) in DMF (5 mL) was added 3,4-dichlorobenzoic acid hydrazide (23 mg, 0.11 mmol), DIPEA (19.5 µL, 0.11 mmol) and HOBt (14.0 mg, 0.10 mmol). The resulting solution was stirred for 5 min prior to the addition of EDCI (23 mg, 1.20 mmol). The reaction mixture was stirred for 16 hr at rt then partitioned between water (10 mL) and dichloromethane (20 mL) on a hydrophobic frit. The aqueous phase was extracted with a further portion of dichloromethane (30 mL) and the combined organics were concentrated in vacuo. Trituration of the resulting residue with ethyl acetate/dichloromethane gave the title compound. $\delta_H$ (d$_6$ DMSO): 12.25 (1H, s), 10.83 (2H, d), 8.17 (1H, s), 7.55-7.97 (3H, m), 7.38 (1H, s), 7.26 (1H, d); m/z (ES+)=383 [M+H]+; RT=3.37 min.

Example 25

5-Chloro-1H-pyrrolo[2,3-c]pyridine-2-carboxylic acid N'-(tertbutyloxycarbonyl)hydrazide

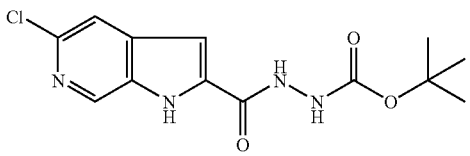

To a solution of 5-chloro-1H-pyrrolo[2,3-c]pyridine-2-carboxylic acid (Preparation 8, 2.05 g, 10.4 mmol) in DMF (30 mL), tert-butyl carbazate (1.38 g, 10.4 mmol), DIPEA (3.5 mL, 20.4 mmol), HOBt (1.58 g, 10.3 mmol) and EDCI (2.54 g, 13.3 mmol) were added successively. The resulting solution was stirred for 12 h at rt before adding water and brine (1:1, 200 mL). The solution was extracted with ethyl acetate (4×50 mL) and the combined organic layers were washed with dilute hydrochloric acid (1N, 50 mL), dilute sodium hydroxide solution (1N, 50 mL) and brine. The organic layer was dried (MgSO$_4$) and concentrated in vacuo to give a solid residue, which was purified by flash chromatography on silica gel (hexane/ethyl acetate, 1:3) to give the title compound. $\delta_H$ (CDCl$_3$): 1.42 (9H, s), 7.19 (1H, s), 7.78 (1H, s), 8.60 (1H, s), 9.28 (1H, br s).

The biological activity of the compounds of the invention may be tested in the following assay systems:

In Vitro GP Activity

Materials

α-D-Glucose-1-Phosphate (disodium salt), Glycogen, D-Glucose, Malachite Green Hydrochloride, Ammonium Molybdate tetrahydrate, BSA, HEPES and rabbit muscle phosphorylase α (P1261) were purchased from Sigma. All other reagents were analytical grade.

Method

Glycogen Phosphorylase Assay In Vitro

An assay for glycogen phosphorylase activity in the reverse direction was developed based on the method described by Engers et al., Can. J. Biochem., 1970, 48, 746-754]. Rabbit muscle glycogen phosphorylase α (Sigma) was reconstituted at a stock concentration of 100 μg/mL in 25 mM Tris/HCl. The pH was measured in a 96-well plate in a final volume of 100 μL containing 50 mM Hepes pH 7.2, 7.5 mM glucose, 0.5 mM glucose-1-phosphate and 1 mg/mL glycogen. After incubation at 30° C. for 30 min, the inorganic phosphate released from glucose-1-phosphate was measured by the addition of 150 μL of malachite green/molybdate solution prepared as follows: 5 mL of 4.2% ammonium molybdate in 4N HCl, 5 mL of 0.045% malachite green, 50 μL of Tween 20. Following a 30 min incubation at rt, the absorbance was measured at 620 nm. For IC$_{50}$ determination, 10 μL of a serial dilution of compound (100M to 0.004 μM) in DMSO was added to each reaction in duplicate with the equivalent concentration of DMSO added to the control uninhibited reaction. Dose response curves were then obtained by plotting % inhibition versus log$_{10}$ compound concentration. IC$_{50}$ is defined as the concentration of compound achieving 50% inhibition under the assay conditions described.

Examples of compounds of the present invention demonstrated efficacy in the above assay with IC$_{50}$ results in the range of better than 100 μM.

The invention claimed is:

1. A compound of formula (I):

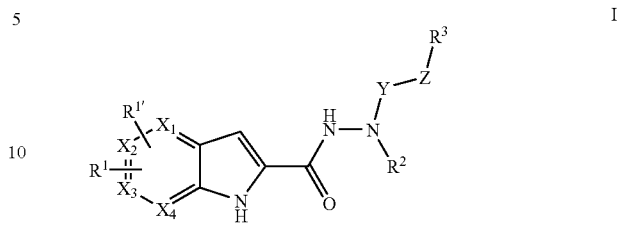

or a pharmaceutically acceptable salt thereof, wherein:
one of $X_1$, $X_2$, $X_3$ and $X_4$ is N and the others are C;
Y is —C(O)—, —S(O)$_2$—, or —C(NH)—;
Z is $C_{1-4}$alkylene, oxygen, —(CH$_2$)$_m$O—, —O(CH$_2$)$_m$—, —NR—, —(CH$_2$)$_m$NR—, —NR(CH$_2$)$_m$—, —(CH$_2$)$_m$S(O)$_2$— or a bond;
m is 1, 2, 3, or 4;
R is $C_{0-4}$alkyl, $C_{0-4}$alkylaryl, or $C_{0-4}$alkylhetaryl;
$R^1$ and $R^{1'}$ are each independently, halogen, hydroxy, cyano, $C_{0-4}$alkyl, $C_{1-4}$alkoxy, fluoromethyl, difluoromethyl, trifluoromethyl, ethenyl, or ethynyl;
$R^2$ is $C_{0-4}$alkyl, COOR$^6$, COR$^6$, $C_{1-4}$alkoxyC$_{1-4}$alkyl-, hydroxyC$_{1-4}$alkyl-, cycloalkylC$_{0-4}$alkyl-, arylC$_{0-4}$alkyl-, or hetarylC$_{0-4}$alkyl-, wherein any of the aryl or hetaryl rings are optionally substituted with 1-2 independent halogen, cyano,C$_{1-4}$alkyl, C$_{1-4}$alkoxy, —N(C$_{0-4}$alkyl)(C$_{0-4}$alkyl), —SO$_2$C$_{1-4}$alkyl, —SO$_2$N(C$_{0-4}$alkyl)(C$_{0-4}$alkyl), hydroxy, fluoromethyl, difluoromethyl, or trifluoromethyl substituents;
$R^3$ is hydrogen, —COOC$_{0-4}$alkyl, C$_{1-4}$alkoxy, C$_{1-4}$alkyl, arylC$_{1-4}$alkylthio-,—C$_{0-4}$alkylaryl, —C$_{0-4}$alkylhetaryl, —C$_{0-4}$alkylcycloalkyl, or —C$_{0-4}$alkylheterocyclyl, wherein any of the rings is optionally substituted with 1-3 independent halogen, cyano, C$_{1-4}$alkyl, fluoromethyl, difluoromethyl, trifluoromethyl, —C$_{0-4}$alkylNHC(O)O(C$_{1-4}$alkyl),—C$_{0-4}$alkylNR$^7$R$^8$, —C(O)R$^9$, C$_{1-4}$alkoxyC$_{0-4}$alkyl-, —COOC$_{0-4}$alkyl, —C$_{0-4}$alkyl-NHC(O)R$^9$, —C$_{0-4}$alkylC(O)N(R$^{10}$)$_2$, —C$_{1-4}$alkoxyC$_{1-4}$alkoxy, hydroxyC$_{0-4}$alkyl-, —NHSO$_2$R$^{10}$, —SO$_2$(C$_{1-4}$alkyl), —SO$_2$NR$^{11}$R$^{12}$, 5- to 6-membered heterocyclyl, phenylC$_{0-2}$alkoxy, or phenylC$_{0-2}$alkyl substituents, wherein phenyl is optionally substituted with 1-2 independent halogen, cyano, C$_{1-4}$alkyl, C$_{1-4}$alkoxy, —N(C$_{0-4}$alkyl)(C$_{0-4}$alkyl), —SO$_2$C$_{1-4}$alkyl, —SO$_2$N(C$_{0-4}$alkyl)(C$_{0-4}$alkyl), hydroxy, fluoromethyl, difluoromethyl, or trifluoromethyl substituents, or two bonds on a ring carbon of the heterocyclyl group optionally can form an oxo (═O) substituent;
or $R^3$ is —NR$^4$(—C$_{0-4}$alkylR$^5$);
$R^4$ is $C_{0-3}$alkyl, —C$_{2-3}$alkyl-NR$^7$R$^8$, C$_{3-6}$cycloalkyl optionally substituted by hydroxyCo$_{0-4}$alkyl- further optionally substituted by hydroxy, C$_{1-2}$alkoxyC$_{2-4}$alkyl-, or C$_{1-2}$alkyl-S(O)$_n$—C$_{2-3}$alkyl-;
n is 0, 1, or 2;
$R^5$ is hydrogen, hydroxyC$_{2-3}$alkyl-, C$_{1-2}$alkoxyC$_{0-4}$alkyl, or aryl, hetaryl, or heterocycle;
wherein a heterocyclic nitrogen-containing R$^5$ ring optionally is mono-substituted on the ring nitrogen with C$_{1-4}$alkyl, benzyl, benzoyl, C$_{1-4}$alkyl-C(O)—, —SO$_2$C$_{1-4}$alkyl, —SO$_2$N(C$_{0-4}$alkyl)(C$_{0-4}$alkyl), C$_{1-4}$alkoxycarbonyl, or aryl(C$_{1-4}$alkoxy)carbonyl; and
wherein the R$^5$ rings are optionally mono-substituted on a ring carbon with halogen, cyano, C$_{1-4}$alkyl-C(O)—, C$_{1-4}$alkyl-SO$_2$—, C$_{1-4}$alkyl, C$_{1-4}$alkoxy, hydroxy, —N(C$_{0-4}$alkyl)(C$_{0-4}$alkyl), hydroxyC$_{0-4}$alkyl-, or C$_{0-4}$alkylcarbamoyl-, provided that no quaternised nitrogen is included; or two bonds on a ring carbon of the heterocyclyl group optionally can form an oxo (=O) substituent;

R$^6$ is C$_{1-4}$alkyl, aryl or hetaryl;

R$^7$ and R$^8$ are independently C$_{0-4}$alkyl, C$_{3-6}$cycloalkyl or CO(C$_{1-4}$alkyl);

R$^9$ is C$_{1-4}$alkyl or C$_{3-6}$cycloalkyl;

R$^{10}$ is C$_{0-4}$ or C$_{3-6}$cycloalkyl; and

R$^{11}$ and R$^{12}$ are independently C$_{0-4}$alkyl or together with the nitrogen to which they are attached may form a 4- to 6-membered heterocycle;

provided there are no nitrogen-oxygen, nitrogen-nitrogen, oxygen-oxygen or nitrogen-halogen bonds in the grouping —Y—Z—R$^3$.

2. A compound according to claim 1, or a pharmaceutically acceptable salt thereof, wherein X$_3$ is N.

3. A compound according to claim 1, or a pharmaceutically acceptable salt thereof, wherein X$_1$ is N.

4. A compound according to claim 1, or a pharmaceutically acceptable salt thereof, wherein Y is —C(O)— or —S(O)$_2$—.

5. A compound according to claim 1, or a pharmaceutically acceptable salt thereof, wherein Z is C$_{1-4}$alkylene, oxygen, —(CH$_2$)$_m$O—, —NR— or a bond.

6. A compound according to claim 1, or a pharmaceutically acceptable salt thereof, wherein R$^1$ and R$^{1'}$ are each independently, hydrogen or halogen.

7. A compound according to claim 6, or a pharmaceutically acceptable salt thereof, wherein one of R$^1$ and R$^{1'}$ is hydrogen and the other is 5-chloro.

8. A compound according to claim 1, or a pharmaceutically acceptable salt thereof, wherein R$^2$ is hydrogen.

9. A compound according to claim 1, or a pharmaceutically acceptable salt thereof, wherein R$^3$ is hydrogen, —NR$^4$R$^5$, —NR$^4$(—C$_{1-4}$alkylR$^5$), aryl, hetaryl, or heterocyclyl wherein any of the rings is optionally substituted as defined in claim 1.

10. A compound selected from:

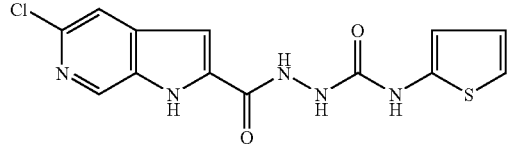

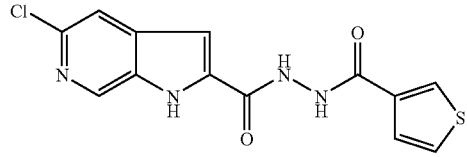

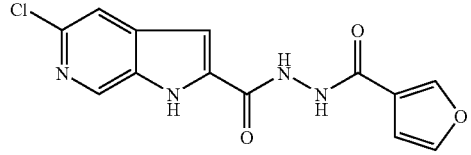

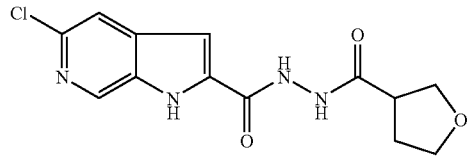

-continued

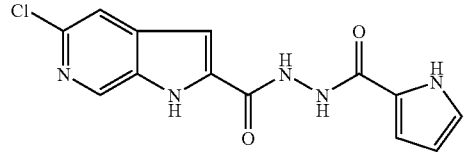

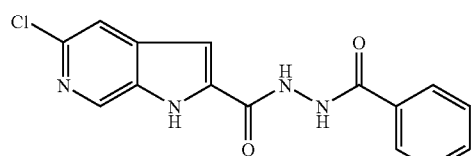

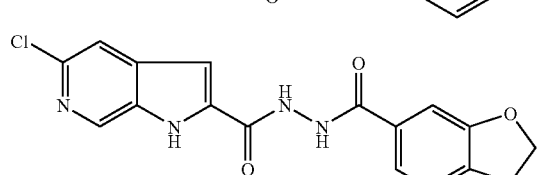

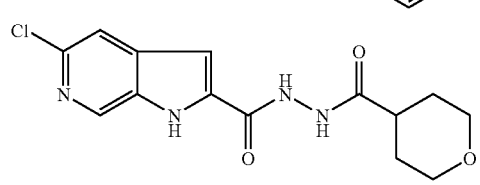

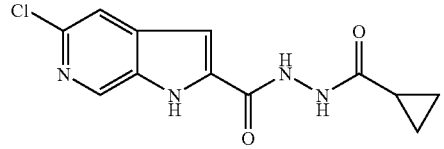

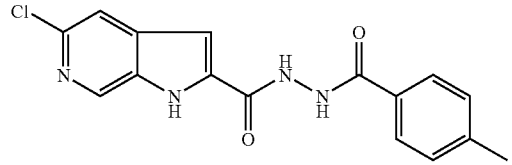

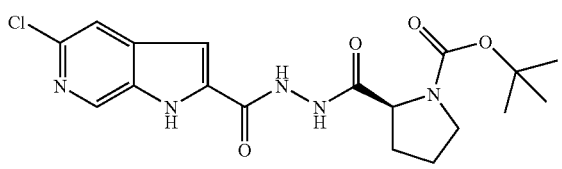

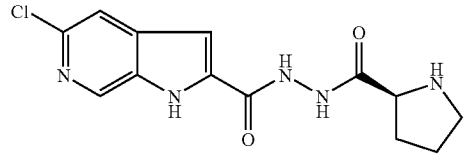

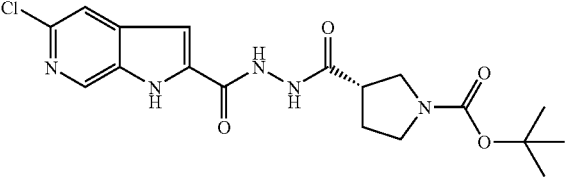

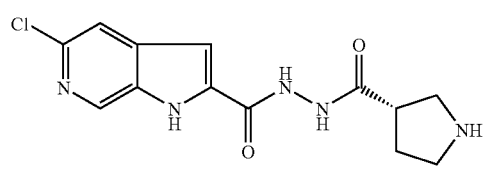

-continued

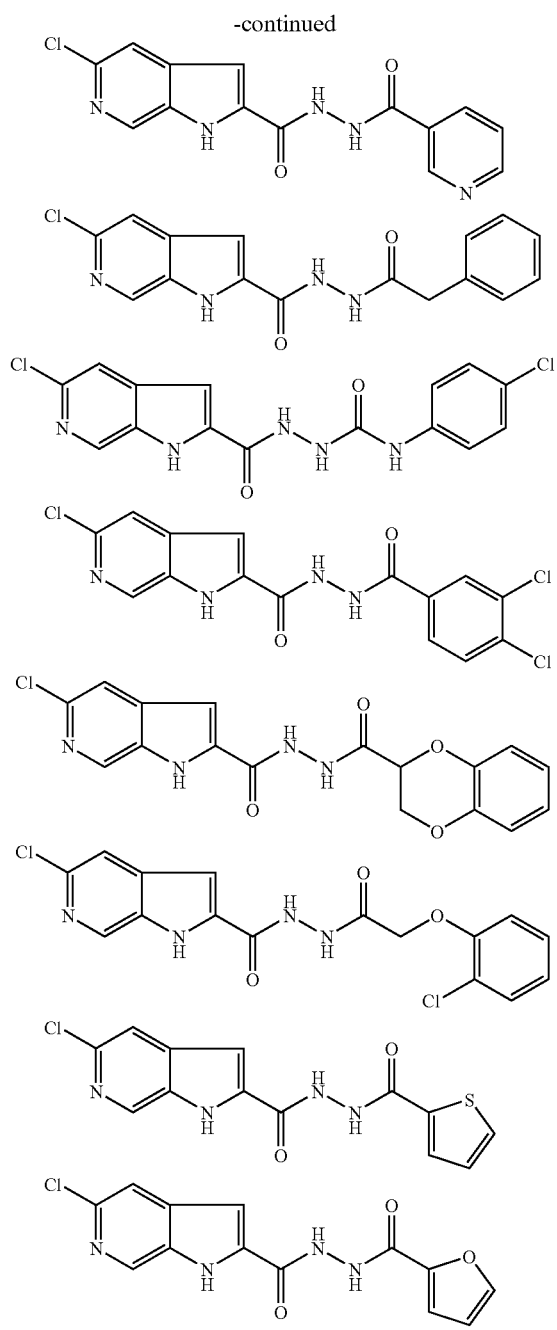

-continued

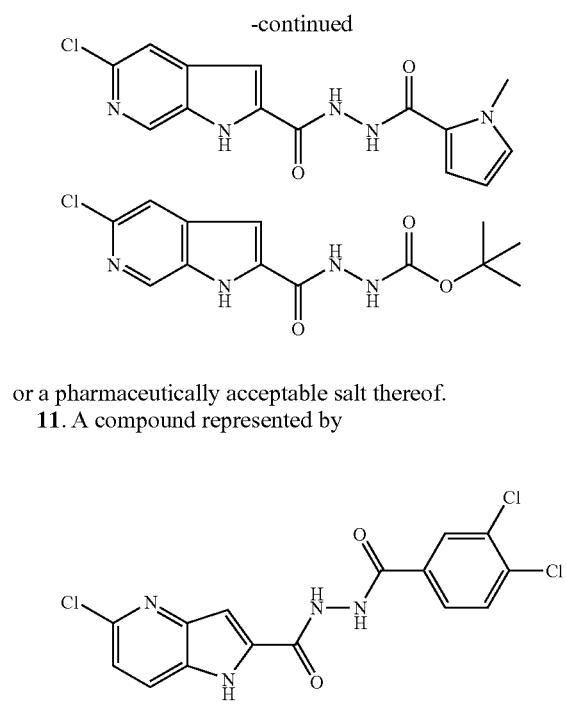

or a pharmaceutically acceptable salt thereof.

11. A compound represented by

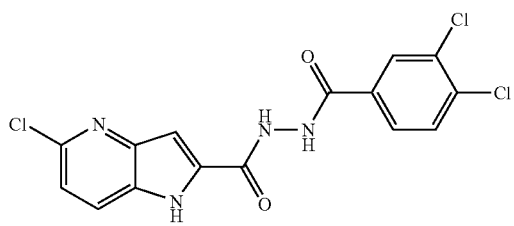

or a pharmaceutically acceptable salt thereof.

12. A pharmaceutical composition comprising a compound according to claim 1, or a pharmaceutically acceptable salt thereof; and a pharmaceutically acceptable carrier.

13. A method for the treatment of hyperglycemia or diabetes comprising a step of administering to a subject in need thereof an effective amount of a compound according to claim 1, or a pharmaceutically acceptable salt thereof.

14. A method for the prevention of diabetes in a human demonstrating pre-diabetic hyperglycemia or impaired glucose tolerance comprising a step of administering to a subject in need thereof an effective prophylactic amount of a compound according to claim 1, or a pharmaceutically acceptable salt thereof.

15. A method for the treatment of hypercholesterolemia, hyperinsulinemia, hyperlipidemia, hypertension, atherosclerosis or tissue ischemia, or achieving cardioprotection or inhibition of abnormal cell growth, comprising a step of administering to a subject in need thereof an effective amount of a compound according to claim 1, or a pharmaceutically acceptable salt thereof.

\* \* \* \* \*